United States Patent [19]
Hutchings

[11] Patent Number: 5,724,265
[45] Date of Patent: Mar. 3, 1998

[54] SYSTEM AND METHOD FOR MEASURING MOVEMENT OF OBJECTS

[76] Inventor: Lawrence J. Hutchings, 18729 Brickell Way, Castro Valley, Calif. 94546

[21] Appl. No.: 570,759

[22] Filed: Dec. 12, 1995

[51] Int. Cl.⁶ .................................................. G01C 22/00
[52] U.S. Cl. .......................... 364/565; 364/410; 364/561; 340/323 R; 235/105
[58] Field of Search .................................. 364/410, 449, 364/450, 561, 565, 569, 556, 559, 143, 443, 460; 128/670, 779; 482/8, 3, 74, 902; 342/52; 324/171; 340/384.71, 323 R; 377/24, 24.2; 73/490; 235/105

[56] References Cited

U.S. PATENT DOCUMENTS

| | | | |
|---|---|---|---|
| 3,789,402 | 1/1974 | Heywood et al. | 340/384.71 |
| 3,797,010 | 3/1974 | Adler et al. | 340/323 R |
| 3,865,305 | 2/1975 | Sampey | 377/24 |
| 4,053,755 | 10/1977 | Sherrill | 364/561 |
| 4,094,199 | 6/1978 | Holdren et al. | 73/517 B |
| 4,180,726 | 12/1979 | DeCrescent | 250/222 R |
| 4,220,996 | 9/1980 | Searcy | 364/561 |
| 4,312,358 | 1/1982 | Barney | 128/670 |
| 4,334,190 | 6/1982 | Sochaczevski | 324/171 |
| 4,371,945 | 2/1983 | Karr et al. | 364/561 |
| 4,387,437 | 6/1983 | Lowrey et al. | 364/561 |
| 4,449,191 | 5/1984 | Mehnert | 364/559 |
| 4,460,823 | 7/1984 | Ruehlmann | 235/105 |
| 4,560,861 | 12/1985 | Kato et al. | 235/105 |
| 4,571,680 | 2/1986 | Wu | 364/410 |
| 4,578,769 | 3/1986 | Frederick | 364/565 |
| 4,627,011 | 12/1986 | Spencer et al. | 364/566 |
| 4,630,226 | 12/1986 | Tanaka | 364/561 |
| 4,703,445 | 10/1987 | Dassler | 364/561 |
| 4,736,312 | 4/1988 | Dassler et al. | 364/561 |
| 4,741,001 | 4/1988 | Ma | 377/24.2 |
| 4,763,287 | 8/1988 | Gerhaeuser et al. | 364/561 |
| 4,821,218 | 4/1989 | Potsch | 364/566 |
| 4,855,942 | 8/1989 | Bianco | 364/561 |
| 4,885,710 | 12/1989 | Hersberger et al. | 364/565 |
| 5,033,013 | 7/1991 | Kato et al. | 364/561 |
| 5,117,444 | 5/1992 | Sutton et al. | 377/24.2 |
| 5,206,652 | 4/1993 | Hoyt et al. | 342/52 |
| 5,245,537 | 9/1993 | Barber | 364/410 |
| 5,396,510 | 3/1995 | Wilson | 372/38 |
| 5,452,216 | 9/1995 | Mounce | 364/449 |
| 5,471,405 | 11/1995 | Marsh | 364/556 |
| 5,516,334 | 5/1996 | Easton | 482/8 |
| 5,524,637 | 6/1996 | Erickson | 128/779 |
| 5,574,669 | 11/1996 | Marshall | 364/569 |
| 5,583,776 | 12/1996 | Levi et al. | 364/450 |

FOREIGN PATENT DOCUMENTS

| | | | |
|---|---|---|---|
| 58-189509 | 11/1983 | Japan | G01C 22/00 |
| 59-202016 | 11/1984 | Japan | G01C 22/00 |
| 60-200119 | 10/1985 | Japan | G01C 22/00 |
| 02121219 | 12/1983 | United Kingdom | G01C 22/00 |

OTHER PUBLICATIONS

Britting, Kenneth R., Inertial Navigation Systems Analysis, Wiley–Interscience, A of John Wiley & Sons, Inc., pp. 1–10, 156–163 (1971, Library of Congress, No. 70–168635).

(List continued on next page.)

*Primary Examiner*—James P. Trammell
*Assistant Examiner*—Cuong H. Nguyen
*Attorney, Agent, or Firm*—Sofer & Haroun, LLP

[57] ABSTRACT

A device that measures the distance traveled, speed, and height jumped of a person while running or walking. Accelerometers and rotational sensors are placed in the sole of one shoe along with an electronic circuit that performs mathematical calculations to determine the distance and height of each step. A radio frequency transmitter sends the distance and height information to a wristwatch or other central receiving unit. A radio frequency receiver in the wristwatch or other unit is coupled to a microprocessor that calculates an output speed based upon step-distance and elapsed time, and the distance traveled of the runner from the sum of all previous step distances. The output of the microprocessor is coupled to a display that shows the distance traveled, speed, or height jumped of the runner or walker.

22 Claims, 5 Drawing Sheets

OTHER PUBLICATIONS

Goldstein, Herbert, *Classical Machanics*, Ch. 4,pp. 124–132, Addison Wesley Publishing, Reading, MA 1956.

Van Bronkhorst, A., Euler Angle Strapped–Down Computer, Advisory Group for Aerospace Research and Development (AGARD), Inertial Navigation Systems and Components, pp. 253–257 North Atlantic Treaty Organization, May 1968.

Casio product, "JC–10–1BV Jog & Walk Calorie", Web site, http://www.starnetinc.com/globalproducts/casio/jc101bv.html, 1997.

Airline International Home Page, "Electronic Pedometer", http://www.ishops.com/airline/el–ped.html, 1997.

Meijer, et al. "Methods to Assess Physical activity with Special Reference to Motion Sensors and Accelerometers", IEEE Trans. on Biomedical Engineering, vol.38, No.3, Mar. 1991.

SYSTEM AND METHOD FOR MEASURING MOVEMENT OF OBJECTS

FIELD OF THE INVENTION

This invention relates generally to the field of measuring instruments and is particularly directed to a system and method for determining the speed, distance traversed, and height jumped by a person while running or walking.

BACKGROUND OF THE INVENTION

In recent years many individuals have mined to their own fitness program of regular jogging. As used herein, jogging is also intended to include running and walking and the words are used interchangeably. Jogging has long been recognized for its therapeutic effects on the body. It purportedly increases cardiopulmonary fitness, helps to lower blood pressure, decreases cholesterol and triglyercides associated with heart disease and reduces weight. Jogging is also one of the easiest exercises to do. It requires no athletic ability and can be done almost any time and any place with a minimum of equipment and without assistance. In more recent times, jogging has also gained acceptance for its recreational value as well and is recognized as a positive factor in promoting psychological well-being.

The popularity of jogging today is well documented by the large numbers of products and literature available to the public. As in many exercise and sporting endeavors, there exists in the prior art a wide variety of devices for aiding those who jog. Many people who run, jog or walk regularly desire to know their progress over time. Therefore, it is desirable to know the accurate distance and speed traveled during an exercise session. This information allows a jogger to monitor his or her progress and accordingly pursue a regular course of exercise designed to enhance performance.

Further, it has become desirable to accurately measure the speed of amateur and professional runners, both in training and during competition. In the prior art, such measurements were made with a stop watch timing the runner over a known distance. Heretofore, it has not been possible to obtain accurate instantaneous speeds of runners or height jumped using the measuring devices currently known in the prior art.

The simplest jogging aids for measuring movements are basic pacing timers such as those disclosed in U.S. Pat. No. 3,540,344 to Veech and U.S. Pat. No. 3,882,480 to Greber. Pacing timers generate a repetitive audio tone signal at selected intervals for pacing the strides of the jogging, where the length of the interval between tones is adjusted to suit the pace of the individual jogger.

There are other running aids known in the prior art such as pedometers as disclosed in U.S. Pat. No. 4,053,755 to Sherrill. These devices usually count the number of steps taken and for a particular stride length, the approximate distance traversed can be determined.

Human speedometers and odometers that measure the speed and distance traveled by a person include devices that utilize ultrasound to measure the distance between each foot such as disclosed in U.S. Pat. No. 4,736,312 to Dassler. Also used is a device that measures the elapsed time of shoe in contact with the ground and converts this to the length of step and speed as disclosed In U.S. Pat. No. 4,578,769 to Frederick.

While pacing timers, pedometers, ultra sound, and elapsed foot-time-distance devices are useful to the runner and walker, they are deficient in several areas. For example, while ultra sound devices can measure the distance between two feet, this is not equivalent to the length of a step or a stride, which is defined as the distance traveled by the same foot from the beginning of a stride till the end of the same stride. For example, the difference between (1) separation between feet, as measured by the ultra sound device, and (2) stride length, is different for each person and will vary for different speeds of running.

Furthermore, devices that employ elapsed-foot-contact-time measurements, have significant errors in measuring stride length. It is known that above a certain speed, stride length begins to increase as speed increases, and the relationship of stride length to speed is not directly proportional, and moreover, is different for each runner. In addition, most of the devices mentioned above require calibration, which may prove to be a difficult task. For example, many of these devices need to be calibrated by the manufacturer or by specially designed equipment.

It is, therefore, a difficult task to determine the correct stride length for an individual runner at various speeds. Thus, pacing timers can provide no more than a constant running pace, and pedometer measurements are only useful as an approximation of distance traversed. Also, ultra sound and elapsed-foot-time-distance devices provide only a rough approximation of actual distance traveled and speed of the person. Also, none of the prior art includes a measurement of height jumped. Running and walking aids known in the prior art are often deficient and cumbersome to use and they often add weight to the runner or walker while providing only marginal utility in terms of the amount of information available and its accuracy.

With the foregoing in mind, the ideal running aid should, therefore: be light in weight; serve a number of useful functions; be inexpensive; provide measurements that are readily available to the user; be reliable and easy to use; and provide accurate measurements of speed, distance traversed, height jumped, and other useful information.

OBJECT OF THE INVENTION

It is the overall objective of this invention to provide a new and improved running and walking measuring system, which overcomes the disadvantages of the prior art devices and substantially increases the amount and accuracy of information available to the jogger.

A specific objective of this invention is to provide a new and improved running and walking measuring system, in which the speed of the runner can be easily and accurately determined.

A further specific objective of this invention is to provide a new and improved running and walking measuring system, in which the distance traversed by the runner can be easily and accurately determined.

Another specific objective of this invention is to provide a new and improved running measuring system, in which the height jumped by the runner or jogger can be easily determined.

A still further objective of this invention is to provide a new and improved running and walking measuring system having the above advantages which is light in weight, relatively inexpensive and convenient to use.

SUMMARY OF THE INVENTION

In accordance with one aspect of the invention, a device for measuring the performance of a runner utilizes accelerometers and rotational sensors to measure the speed, distance traveled, and height jumped of a person. It may be preferably placed in the sole of a shoe and information signals may be transmitted to the user's watch for display. An indication signal may be configured to reset measurement values to zero coordinates with each step taken, and the system records accelerations relating to the movement of the foot to the next step. The accelerations recorded are multiplied by appropriate cosine and sine values of angles of rotation of the foot, and integrated twice to obtain displacement of each step. Time is incorporated with the acceleration to perform the integration. Once the length of steps is determined, the elapsed time is used to obtain the speed of the person, and the sum of the step lengths is used to obtain the distance traveled. The maximum value of the vertical displacement is used to determine the height jumped. One set of three-component linear accelerometers and one set of three-component rotational sensors are necessary to fully resolve the absolute motion of a person from the motion of the foot.

According to another aspect of the invention, substantially satisfactory measurements may be obtained with two accelerometers and one rotational sensor; or the system may be attached to the top portion of the user's shoe, instead of installation inside the sole of the shoe.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof may best be understood by reference to the following detailed description when read with the accompanying drawings in which:

DETAILED DESCRIPTION OF THE INVENTION

Figure 1:
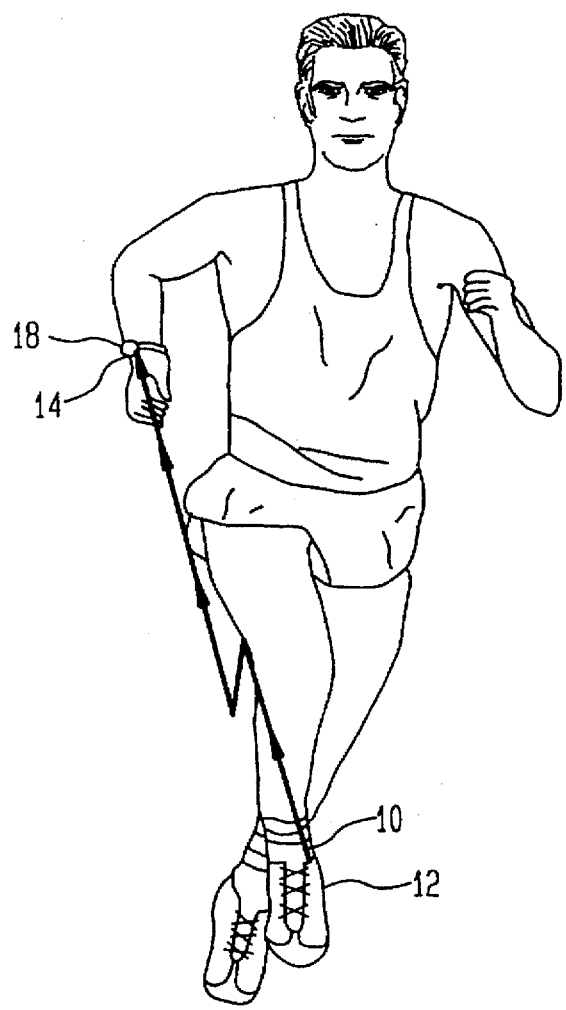
FIG. 1 illustrates one embodiment of the invention as employed by a user.

FIG. 1 shows an embodiment of a measuring system 10 as employed by a user, although the invention is not limited in scope to the location of different components of the system as illustrated herein. The shoe of the user may include interrelated elements such as linear accelerometers; rotational sensors; a microprocessor to calculate the distance and height of each step; a foot impact switch; battery; and a radio transmitter 12, as will be explained in more detail below.

As shown in FIG. 1, the user may wear a hand display having a radio receiver 14. The radio receiver may alternately be located at a remote site so that the performance of the runner can be monitored by another person. Incorporated into the receiving unit may be a microprocessor for processing the received signals into the speed of the runner, the distance traversed and the height jumped. The processed information may be selectively displayed on display 18. The hand display may also perform other functions, for example, it may selectively display normal watch functions, such as time of day, date, alarm and stop watch signals.

Figure 2:
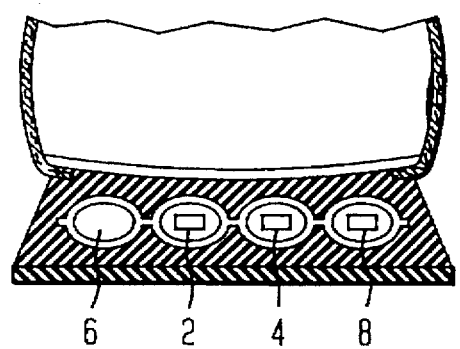
FIG. 2 illustrates the location of the system's components in the sole of the shoe, in accordance with an embodiment of the invention.

FIG. 2 shows one possible location of different components of the measuring system in the sole of the user's shoe. However, the invention is not limited in scope in this respect, and, various components of the system in accordance with the present invention may be implemented in a variety of arrangements. Accelerometers 2, rotational sensors 4, and a contact switch 8 are preferably placed in the ball-of-the-foot portion of the sole of the shoe so that they may come in contact with the ground for each step during either walking or running. As it will explained in more detail below, the measuring system in accordance with the present invention may also operate without contact switch 8. Measuring system 10 may include three rotational sensors 4, each configured to measure the angle of the user's foot with respect to a reference frame as will be explained in more detail below. Rotational sensors 4 are well known, such as those provided by AMP model numbers ACH-04-08. Each rotational sensor converts the measured angle into a corresponding signal, which is employed by a microprocessor 6 to calculate information related to the user's movements, such as user's speed, distance traveled and the height jumped. It will be appreciated that the present invention is not limited in scope to the components illustrated in FIG. 2. For example, instead of contact switch 8, other means may be employed so as to generate a signal to indicate the beginning of each step.

Measuring system 10 preferably includes three accelerometers 2, each configured to measure the acceleration of the user's foot with respect to a reference frame as will be explained in more detail below. The accelerometers may also be located in the sole of the user's shoe. Accelerometers 2 are well known, such as those provided by Analog Devices model ADXL05. Each accelerometer may convert the measured acceleration into a corresponding signal, which may be preferably employed by microprocessor 6 to accomplish movement measurements.

Also, other components may be separated and placed in another portion of the shoe. For example, the measuring system may be placed at another location of the shoe.

Figure 3:
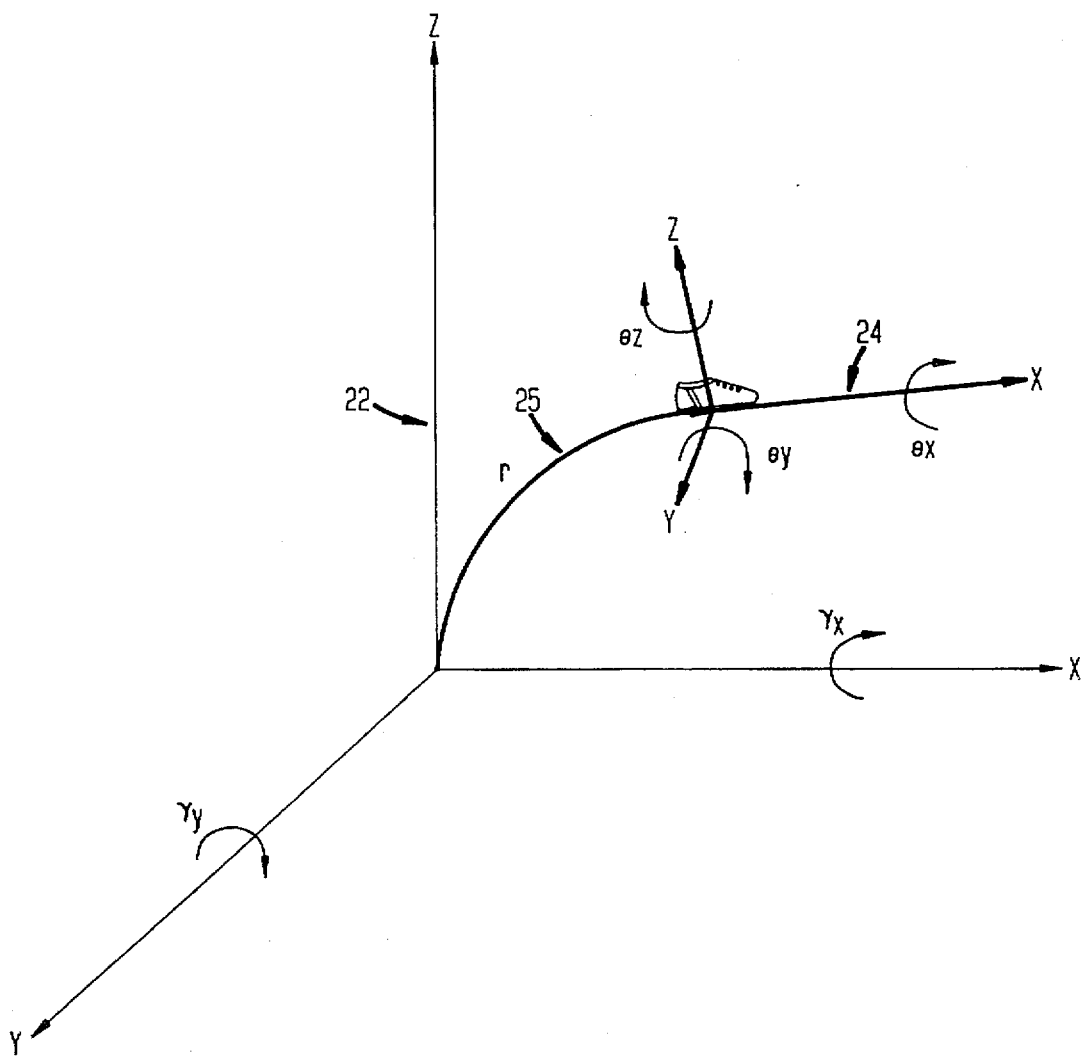
FIG. 3 is a coordinate system for the reference frame of the stationary ground, and the vectors of linear and rotational motion that are necessary to determine motion of the foot in accordance with one embodiment of the invention.

FIG. 3 illustrates a plot of the coordinate systems necessary to resolve step length and height. In the present context, a first coordinate system, such as (x,y,z) 22, is referred to as the reference frame coordinate system of the stationary ground. $(Y_x, Y_y)$ are the rotational coordinates about x and y axis of the reference frame. In one embodiment of the invention, rotation about the z axis may not be measured. These values advantageously indicate the slope of the ground at the beginning of the step. Preferably, the reference frame coordinate system is reset at the initiation of a new step and remains stationary throughout the time the same foot leaves and touches the ground again. The orientation of the reference frame coordinate system with respect to the foot is arbitrary, but it is preferably selected so that at the beginning of the step the positive x direction may be aligned with the axis of the sole of the shoe, the positive y axis may be in the same plane as the sole and at right angles to the x axis, and the positive z axis may be normal to the plane of the sole of the shoe. The arrows in FIG. 3 indicate the direction of positive motion. The length and height of each step with respect to this coordinate system may be measured in accordance with the present invention as explained in more detail hereinafter.

FIG. 3 also illustrates a second coordinate system, such as (X,Y,Z) 24, referred to as the translational coordinate system of the linear accelerometers. This coordinate system moves with the foot and may be centered at the location of the sensors. FIG. 3 further illustrates rotational coordinates, such as ($\theta_x, \theta_y, \theta_z$) about the axes X, Y and Z. These rotational coordinates may be employed advantageously to keep track of the orientation of the (X,Y,Z) coordinate system relative to the (x,y,z) coordinate system, as will be explained below, and to resolve the accelerations along the reference frame.

In FIG. 3, an exemplary foot is shown part way through a step that moves along a trajectory r such as 25. The orientation of the translational coordinate system with respect to the foot is the same as described for the reference frame, but moves with the foot. Preferably, the reference and translational coordinate systems may be aligned together every time a new step is initiated.

Figure 4:
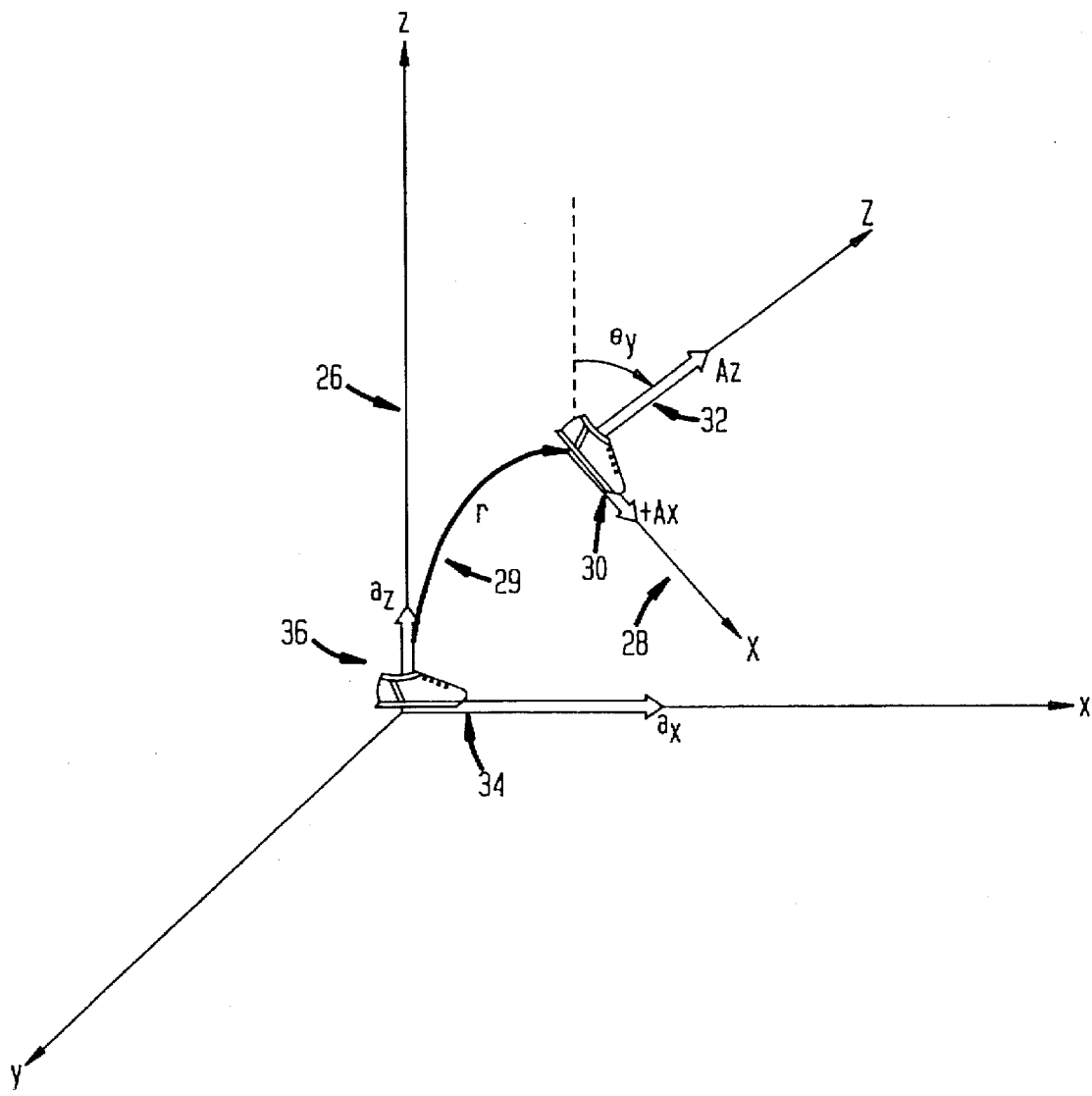
FIG. 4 is a side view diagram of the foot during running, illustrating information employed to resolve step length in two dimensions in accordance with one embodiment of the invention.

FIG. 4 illustrates an example of a motion of the foot and how the length of the step is resolved for a motion in one plane, along two dimensions (here, the plane of the paper), and for a step along a horizontal surface. The reference frame coordinate system 26 is that described as 22 in FIG. 3, and the translational coordinate system 28 is that described as 24 in FIG. 3. The foot is shown part way through a step having moved along trajectory r such as 29. The translational coordinate system is moving along trajectory 29, as described in FIG. 4.

FIG. 4 also illustrates acceleration vectors (Ax, Az) in the translational coordinate system. These accelerations are represented by arrows aligned along the X and Z axes of the translation coordinate system, respectively. The length of the arrows represent the amount of acceleration for each component (30 and 32, respectively). The angle of rotation about the y axis relative to the reference frame coordinate system is $\theta_y$. From these components of motion the acceleration relative to the reference frame coordinate system can be resolved. This is shown as ax and az in the reference flame (34 and 36, respectively).

The amount of acceleration and its direction (a vector solution) is preferably employed to keep track of forward and reverse motions of the foot. For example, if motion remains in the (z,x) plane and the surface is horizontal (FIG. 4), then (1) $ax = Ax \cos \theta_y + Az \sin \theta_y$ (2) $az = -Ax \sin \theta_y + Az \cos \theta_y - g$ Where g is the acceleration due to gravity, which is preferably considered as a factor due to the use of accelerometers. Gravity may be assumed to be a constant as explained in more detail below. Here, acceleration az is assumed to be vertical and aligned with the orientation of gravity. Acceleration az may be aligned at an angle from the direction of gravity, such as on a hill, as explained in more detail below. The −g factor added to the az component of equation 2 is to balance the effect of gravity on an inertial linear accelerometer. For example, if the user of the system is standing still, $\theta_y=0$ and $Az=+g$, then $az=0$. If the user is moving up at g, Az will read 2g, and az=g. If the user moves down at g and $\theta_y=180$, Az=0, and az −g. For forward horizontal motion, for example, $\theta_y=45°$, Az and Ax would be positive and substantially equal from motion, but there would be an added positive g cos $\theta_y$ component added to Az and an added negative g sin $\theta_y$ component added to Ax, and their sum would be such that az=0. The length of the step is obtained by integration as discussed in reference with FIG. 5.

Figure 5:
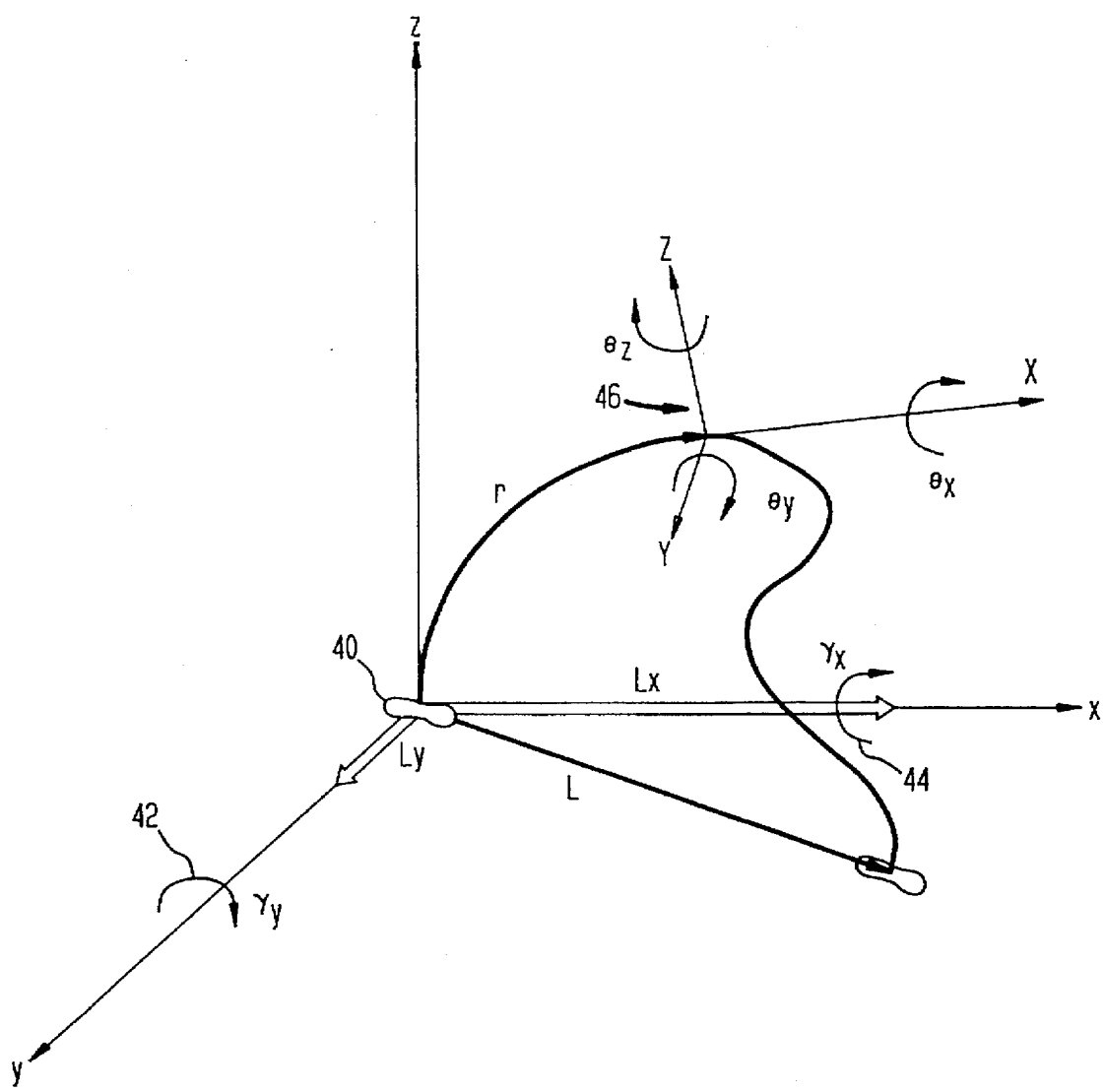
FIG. 5 is a vector diagram illustrating output acceleration, velocity and displacement of one embodiment of the invention during running.

FIG. 5 shows the elements that may be employed to obtain a complete solution of the foot motion in three dimensions. The reference frame is established from the foot contact at the beginning of a step 40. The reference frame z axis may not be aligned with the direction of gravity if the ground (x,y plane) is not horizontal. $\gamma_y$ 42 is the angle of the x axis from the horizontal plane, and $\gamma_x$ 44 is the angle of the y axis from the horizontal plane. These values are unknown, as they depend on the slope of the ground at the beginning of each step, and are calculated by measuring system 10, as explained below. At any point along the trajectory r, the components of motion in the reference frame can be determined from the linear accelerometers and rotational sensors in the translational coordinate system 46.

(3) $ax = [\cos \theta_x \cos \theta_y \cos \theta_z]Ax - [\sin \theta_x \cos \theta_y \cos \theta_z + \cos \theta_x \sin \theta_z]Ay + \sin \theta_y \cos \theta_z Az$ (4) $ay = [\cos \theta_x \cos \theta_y \sin \theta_z + \sin \theta_x \cos \theta_z]Ax - [\sin \theta_x \cos \theta_y \sin \theta_z - \cos \theta_x \cos \theta_z \cos \theta_z]Ay + \sin \theta_y \sin \theta_z Az$ (5) $az = -\cos \theta_x \sin \theta_y Ax - \sin \theta_x \sin \theta_y Ay + \cos \theta_y Az$ As explained in reference with FIG. 4, the terms involving gravity g counteract the accelerations in gravity recorded by the inertial linear accelerometers. The values for $\gamma_x$ and $\gamma_y$ may be determined at the initiation of each step, and are substantially equal to zero for a substantially horizontal surface. At this time the proportion of gravity recorded by the accelerometers is related, among other things, to the angle from the vertical coordinate (as resolved by an accelerometer such as the ADXL05, from Analog Devices).

(6) $\gamma_x = \sin^{-1} (Ax/g)$ (7) $\gamma_y = \sin^{-1} (Ay/g)$

In order to assure accurate measurements, the accelerometers employed in the present invention are desired to be properly calibrated. The embodiments described herein may be conveniently calibrated in accordance with the present invention. This follows because gravity g only varies by less than 0.3% throughout the surface of the earth, and provides a substantially constant value in a direction substantially aligned towards the center of the earth. Therefore, an accelerometer employed in accordance with the present invention must generate an acceleration signal substantially equal to gravity g, when the user's foot is resting on a surface. It will be appreciated that an embodiment in accordance with the present invention may be configured so as to advantageously reset the value generated by the accelerometers to substantially represent gravity, g, when the user's foot is resting on a surface. As such, the accelerometers employed in accordance with the present invention may remain substantially calibrated at all times.

Since the accelerometers and rotation sensors are connected to a timing device, their values may be known as a function of time. The horizontal and vertical displacement may then be obtained by integrating by time as they traverse the path:

(8) $Lx = \iint ax(t) dt^2$ $$(9)\ Ly = \iint ay(t)dt^2$$

$$(10)\ Lz = \iint az(t)dt^2$$

The integration is performed twice to obtain Lx, Ly, Lz shown in the equations. Lz would be zero if the ground remained at the slope of the beginning of the step, and would be significant if a person, for example, climbed a step. To obtain the length of the step, $$(11)\ L = \sqrt{Lx^2 + Ly^2 + Lz^2}$$

The maximum height H jumped is, $$(12)\ H = max(Lz)$$

Figure 6:
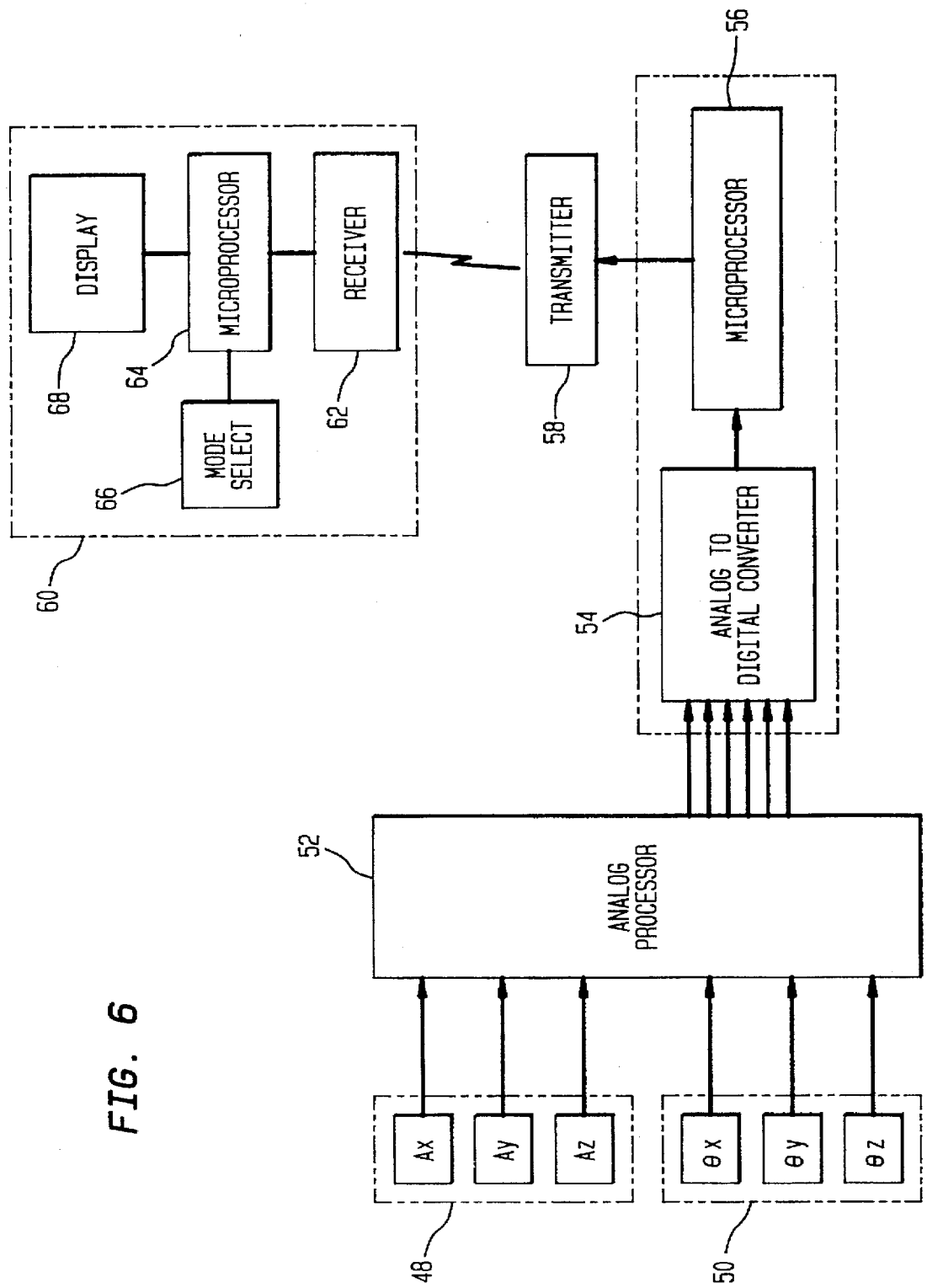
FIG. 6 is a block diagram of the electronic units necessary to solve equations for step length in accordance with the invention.

FIG. 6 is a block diagram of the components employed to solve the equations, although the invention is not limited in scope in this respect. Therefore, any hardware or software system configured to solve the above equations to measure the length of each step and the height jumped may be employed. In FIG. 6, unit 48 may preferably contain the linear accelerometers employed to measure accelerations Ax, Ay and Az and frequency filters (not shown). Such filters may be used to reduce high frequency components in measured acceleration signals. The linear accelerometers are configured to measure accelerations in three dimensions, along the direction of the foot as it travels during each step.

Unit 50 may preferably contain rotational sensors employed to measure θx θy and θz signals. Thus the rotational sensors provide the angle of rotation along each axis of the translational coordinate. The output terminals of traits 48 and 50 are coupled to input terminals of a processor 52. Processor 52 may be employed to make the calculations necessary to solve equations 3–7 mentioned above. For example, the sine and cosine of each measured angle may be computed by processor 52. The sine and cosine value signals are then coupled to input terminals of unit 54.

Unit 52 may contain multipliers and adder processors to solve equations 3–7 in analog format. In accordance with another embodiment of the invention, processor 52 may process the received signals digitally by employing an analog to digital converter and a microprocessor that calculates equations, 3–7. Yet, in accordance with another embodiments of the invention, the ouptut terminals of units 48 and 50 may be coupled directly to a microprocessor 56, via an analog to digital converter 54. Analog to digital converter 54 may be a separate integrated circuit, such as one provided by Linear Technology LTC 1098. In another embodiment of the invention, analog to digital converter 54 may be part of microprocessor 56, such as one provided by Motorola MC68HC11E9.

Microprocessor 56 is preferably configured to measure the distance L traversed after each step and the maximum height H jumped during that step. It will be appreciated that these measurements may be employed in either analog or digital format.

In accordance with one embodiment of the invention, a foot switch (not shown) may be employed so as to reset the accelerometers and rotational sensors contained in units 48 and 50, when the user's shoe contacts the ground. Information relating to the length and height of a step, and the contacts with ground may then be transmitted by transmitter 58 to a remote receiver unit 60. However, the invention is not limited in scope in this respect. For example, instead of a foot switch, the accelerometers or the rotational sensors may be configured to reset themselves, whenever their output signal levels indicate that the user's foot has touched the running surface again.

Unit 60 is the remote device, which may be located in the user's wrist watch, and contains a receiver 62, a microprocessor 64, a mode select switch 66 and a display 68. Transmitter 58 includes a means for encoding the output signals provided by a microprocessor 56 into a transmitted signal. Transmitter 58 may also be of the type already known in the art such as the RF Monolithics model HX2000. Transmitter 58 may operate on any frequency selected and use amplitude or frequency modulation. The transmitted signal from transmitter 58 is received and decoded by receiver 62. Receiver 62 may also be of the type known in the prior art such as the RF Monolithics model RX2010. Receiver 62 may also be selectively tuned to receive the signals of several different transmitters operating on different frequencies so that the performance of several runners may be monitored from a remote location. Microprocessor 64 may be selected from various microprocessors known in the prior art, such as Motorola model MC68HC05L1.

A typical run mode sequence will now be described with reference to FIG. 6. Mode select unit 66 is employed at the start of the run or jog by depressing an appropriate switch, not shown, which is coupled to microprocessor 64 through an input switch control logic interface. As the shoe of the runner comes into contact with the surface, a first output signal is generated by accelerometers contained in unit 48 representing that a foot of the runner is in contact with the surface. Unit 52 begins to calculate the initial orientation of the user's foot along the reference coordinate in accordance with equations (6) and (7).

Thereafter unit 48 generates acceleration signals along the translational coordinates. Rotational sensors contained in unit 50 begin to track the rotation of the user's foot along the translational coordinate system. Thereafter, unit 52 measures instantaneous acceleration of the foot along the reference coordinates as the foot travels in the air and contacts the surface again. Unit 54 receives these acceleration signals and unit 56 calculates the length of each step by integrating the acceleration signals. Unit 56 also calculates the height jumped by obtaining the maximum length measured along the z axis of the reference coordinate system. The output signals are coupled to RF transmitter 58 and transmitted to receiver 62. The signals received by receiver 62 are coupled to microprocessor 64. The microprocessor interface converts the output of a microprocessor to signals suitable to drive display 68.

Speed is continuously calculated by measuring the distance of each step and is instantaneously available for display. Microprocessor 64 also maintains running elapsed time. Microprocessor 64 may be configured to calculate distance traversed by summing the length of all steps taken. It may further be configured to calculate the instantaneous and the average speed of the user. The running elapsed time, the distance traversed and the speed may be selectively displayed on display 68. These values may also be stored in a non-volatile memory (not shown) associated with microprocessor 64 for virtually an indefinite period of time.

For calibration purposes, microprocessor 56 may be desirably configured to monitor the value of signals provided by accelerometers of unit 48. Whenever it is determined that the user's foot is on the running surface, the value of these signals may correspond to gravity, g. If, however, the value of the these signals does not correspond to gravity, g, microprocessor 56 may provide a feedback signal so as to reset the values of the accelerometers to provide a desired signal representing gravity, g.

In the watch mode, microprocessor 64 selectively provides to display 68, normal watch functions such as time of day, date, an alarm signal when a preselected time occurs. Obviously, many modifications and variations of the above preferred embodiment of the invention will become apparent to those skilled in the art from a reading of this disclosure. For example, a less expensive embodiment may be implemented where all electronic components are disposed on the shoe. In that case, there may be no desire for a transmitter and a receiver circuit. It may also be possible to combine the functions performed by microprocessors 56 and 64 into one microprocessor, such as a Motorola model MC68HC05L. In the alternative it is also possible to combine the functions performed by signal processor 52, and microprocessors 56 and 64 into one such microprocessor.

It should be realized that the invention is not limited to the particular embodiment disclosed, but its scope is intended to be governed only by the scope of the appended claims.

I claim:

1. A system for measuring the speed of a person, said system comprising:
   a plurality of accelerometers and rotational sensors disposed in the shoe of said person, said accelerometers configured so as to provide acceleration signals corresponding to accelerations associated with the movement of said shoe as said person takes a step, said rotational sensors configured so as to provide angular signals corresponding to the angle of said shoe about an axis of a three dimensional translational coordinate;
   a calculator coupled to said accelerometers and said rotational sensors configured so as to receive said acceleration signals and said angular signals, said calculator adapted to measure the distance traversed during each step and the speed of said person.

2. The system in accordance with claim 1 further comprising a foot contact sensor adapted to generate an indication signal when a foot of the user is in contact with the surface.

3. The system in accordance with claim 2, wherein said calculator further measures the height jumped during each step.

4. The system in accordance with claim 3 further comprising a transmitter configured so as to receive length and height signals from said calculator, said transmitter further configured to transmit said length and height signals to a remote location.

5. The system in accordance with claim 4 wherein said accelerometers are configured to be calibrated when said user's shoe is resting on a surface.

6. The system in accordance with claim 4 wherein said remote location comprises:
   a receiver adapted to receive said transmitted length and height signals;
   a processor coupled to said receiver, said processor configured so as to calculate the total length traversed by said user and generate a corresponding output distance signal, said processor further adapted to generate a height jumped signal.

7. The system in accordance with claim 6, wherein said processor further calculates the instantaneous and average speed of said user and generates a corresponding output speed signal.

8. The system in accordance with claim 7, wherein said processor includes a timer means for producing output time signals representing the date, time of day and the time elapsed from a predetermined time, said output time signal being selectively provided to a display means, said display means further comprising means for displaying said date, said time of day and said elapsed time in accordance with said output time signals.

9. The system in accordance with claim 8 wherein said processor further comprises means for timing a running elapsed time and generating a signal representing the time elapsed from the beginning of the run.

10. The system in accordance with claim 9 wherein said output speed signal, said running elapsed time signal, said output distance signal and said height jumped signal are stored for a virtually indefinite period of time and selectively displayed.

11. A system for measuring the speed of a runner, said system comprising:
   an accelerometer unit disposed in a shoe of said runner, said accelerometer unit containing a plurality of accelerometers configured to measure the acceleration associated with the movement of said shoe along a translational coordinate defined by the movement of said shoe, said accelerometers further configured to generate acceleration signals corresponding to said measured accelerations;
   a rotational sensor unit disposed in said shoe, said rotational sensor unit containing a plurality of rotational sensors configured so as to provide angular signals corresponding to the angle of rotation of said shoe about each one of said translational coordinates;
   a first calculator unit coupled to said accelerometer unit and said rotational sensor unit configured so as to receive said acceleration signals and said angular signals, said calculator adapted to measure the instantaneous accelerations of said shoe with respect to a reference coordinate defined by said shoe while in contact with a surface;
   a second calculator unit coupled to said first calculator unit configured so as to receive said instantaneous accelerations, said second calculator adapted to measure the length of each step and the height jumped by said person.

12. The system in accordance with claim 11, wherein said accelerometer unit contains three accelerometers each configured to measure accelerations $A_x$, $A_y$, and $A_z$ along X,Y, and Z coordinates of said translational coordinate system.

13. The system in accordance with claim 12, wherein said rotational sensor unit contains three rotational sensors each configured to measure angular signals $\theta x$, $\theta y$ and $\theta z$ corresponding to the angle of rotation of said shoe about the respective X, Y, and Z axis of said translational coordinate system.

14. The system in accordance with claim 13, wherein said first calculator derives acceleration signals along said reference coordinate system in accordance with $$ax=[\cos\theta_x \cos\theta_y \cos\theta_z - \sin\theta_x \sin\theta_z]Ax - [\sin\theta_x \cos\theta_y \cos\theta_z + \cos\theta_x \sin\theta_z]Ay + \sin\theta_y \cos\theta_x Az$$

$$ay=[\cos\theta_x \cos\theta_y \sin\theta_z + \sin\theta_x \cos\theta_z]Ax - [\sin\theta_x \cos\theta_y \sin\theta_z - \cos\theta_x \cos\theta_z]Ay + \sin\theta_y Az$$

$$az=-\cos\theta_x \sin\theta_y Ax - \sin\theta_x \sin\theta_y Ay + \cos\theta_y Az$$

wherein ax is acceleration along the x axis of said reference coordinate, ay is acceleration along the y axis of said reference coordinate, az is acceleration along the z axis of said reference coordinate.

15. The system in accordance with claim 14 wherein said first calculator derives said $\gamma_x$ and $\gamma_y$ angles in accordance with $$\gamma_x = \sin^{-1}(Ax/g)$$

$\gamma_y = \text{Sin}^{-1} (Ay/g)$ wherein Ax is the extent of acceleration along the X axis of said translational coordinate and Ay is the extent of gravity along the Y axis of said translational coordinate at the beginning of each step.

16. The system in accordance with claim 15, wherein said accelerometers are configured to be calibrated when said user's shoe is resting on a surface.

17. The system in accordance with claim 16, wherein said second calculator derives the length of each step L and the height H jumped during each step in accordance with $$Lx = \iint ax(t)dt^2$$

$$Ly = \iint ay(t)dt^2$$

$$Lz = \iint az(t)dt^2$$

$$L = \sqrt{Lx^2 + Ly^2 + Lz^2}$$

$$H = max(Lz)$$

where Lx, Ly and Lz are respectively the length of each step along the reference frame coordinates.

18. A method for measuring the distance traveled by a runner comprising the steps of:

measuring the acceleration associated with the movement of a shoe of said runner along a translational coordinate defined by the movement of said shoe;

measuring the angle of rotation of said shoe about each one of said translational coordinates;

calculating instantaneous accelerations of said shoe with respect to a reference coordinate defined by said shoe while in contact with a surface; and calculating the length of each step and the height jumped by said person in accordance with said calculated instantaneous accelerations.

19. The method in accordance with claim 18 further comprising the step of generating an indication signal when said shoe of said runner contacts the running surface.

20. The method in accordance with claim 19, further comprising the step of repeating said measuring and calculating steps upon detecting said indication signal.

21. The method in accordance with claim 20, further comprising the step of accumulating each calculated step length to measure the total distance traveled by said runner.

22. The method in accordance with claim 21, further comprising the step of calculating the instantaneous and average speed of said runner.

* * * * *